US006977179B2

(12) United States Patent
Rue et al.

(10) Patent No.: US 6,977,179 B2
(45) Date of Patent: Dec. 20, 2005

(54) METHOD AND APPARATUS FOR MEASURING THE HEATING VALUE OF A SINGLE OR MULTI-COMPONENT FUEL GAS

(75) Inventors: David M. Rue, Chicago, IL (US); John Charles Wagner, La Grange, IL (US); Serguei Zelepouga, Mount Prospect, IL (US)

(73) Assignee: Gas Technology Institute, Des Plaines, IL (US)

( * ) Notice: Subject to any disclaimer, the term of this patent is extended or adjusted under 35 U.S.C. 154(b) by 78 days.

(21) Appl. No.: 10/804,291

(22) Filed: Mar. 19, 2004

(65) Prior Publication Data

US 2005/0208672 A1 Sep. 22, 2005

(51) Int. Cl.⁷ .............................................. G01N 21/76
(52) U.S. Cl. ...................... 436/143; 436/155; 436/172; 250/361 C
(58) Field of Search ............................ 422/52; 436/25, 436/139–143, 155, 159, 164, 172; 250/458.1, 250/459.1, 361 C

(56) References Cited

U.S. PATENT DOCUMENTS

| | | | | |
|---|---|---|---|---|
| 3,950,101 A | | 4/1976 | Dewey, Jr. | |
| 4,097,239 A | * | 6/1978 | Patterson | 436/106 |
| 4,978,367 A | * | 12/1990 | Green et al. | 44/281 |
| 4,981,652 A | * | 1/1991 | Ratfisch | 422/54 |
| 5,822,058 A | | 10/1998 | Adler-Golden et al. | |
| 5,882,115 A | * | 3/1999 | Vander Heyden et al. | 374/37 |
| 6,157,455 A | | 12/2000 | Pinvidic et al. | |
| 6,536,946 B1 | * | 3/2003 | Froelich et al. | 374/36 |
| 6,555,820 B1 | * | 4/2003 | Tacke et al. | 250/339.01 |
| 6,579,722 B1 | * | 6/2003 | Collins et al. | 436/172 |

FOREIGN PATENT DOCUMENTS

WO      WO 92/07249      * 4/1992

OTHER PUBLICATIONS

Hutte, R. "New Instrumental Technique for the Analysis of High Energy Content Fuels" Chemical Abstracts, vol. 116 (1992) abstract No. 217711.*

* cited by examiner

*Primary Examiner*—Jeffrey R. Snay
(74) *Attorney, Agent, or Firm*—Mark E. Fejer

(57) ABSTRACT

A method for determining the heating value of a fuel gas or fuel gas mixture in which the chemiluminescense intensity of at least one chemical bond in a known volume of the fuel gas or mixture is measured. Based upon the results of the measurement(s), the amount of the at least one chemical bond in the known volume of the fuel gas or mixture is determined. Having determined the amount of the at least one chemical bond, the heating value of the fuel gas or mixture can be determined.

20 Claims, 2 Drawing Sheets

METHOD AND APPARATUS FOR MEASURING THE HEATING VALUE OF A SINGLE OR MULTI-COMPONENT FUEL GAS

BACKGROUND OF THE INVENTION

1. Field of the Invention

This invention relates to a method and system for determining the energy content or heating value of a fuel gas from the chemiluminescense spectra of excited bonds in that fuel gas.

2. Description of Related Art

A key aspect of efficient and cost-effective use of fuel gases such as natural gas and vaporized liquefied natural gas (LNG) is the ability to accurately determine the energy content or heating value thereof in real-time and at low cost. Commercially available heating value sensors rely upon calorimetric or gas chromatographic processes. These processes are cumbersome and costly, and they require regular calibration.

It is well known that spectroscopy can be used to examine a gas or gas mixture. In accordance with one known method, a known light source is passed through a gas or gas mixture and a detector is used to determine the wavelengths at which light is absorbed by the gas or gas mixture. Every chemical compound has a unique absorption "signature" and specific wavelengths as a function of temperature and pressure. By collecting a spectrogram over an appropriate range of wavelengths, the full absorption signature for the gas mixture can be acquired. The preferred band for examination is most commonly in the near to mid-infrared at wavelengths between 1000 and 5000 nm. This spectrogram can then be mathematically deconvoluted to determine the species present and the concentrations of those species.

Absorption spectroscopy as a means for determining the heating value of a fuel gas or gas mixture is also well-known. For example, U.S. Pat. No. 3,950,101 teaches a spectrophotometric method for measuring the heating value of a mixture of substances comprising a gaseous fuel, which method is based upon the recognition that within certain wavebands the mixture exhibits a correlation between heating value and the strength of radiant energy absorption. The method includes measuring the strength of radiant absorption of a sample of the mixture illuminated by a radiant energy source having known spectral characteristics. The method relies upon the recognition that at least one particular waveband exists within which more than one constituent of the mixture exhibits radiant absorption in proportion to their characteristic heating value. For example, in a waveband centered near 6.83 microns, the common paraffin hydrocarbons found in natural gas, except methane, exhibits radiant absorption in approximately linear proportion to their heating value.

U.S. Pat. No. 6,157,455 teaches a method of determining the calorific value of natural gas optically and in real-time by measuring the absorption of a light beam by the components of the gas, in which the gas is illuminated by a light beam of predetermined characteristics, the intensity of the light beam is measured after it has passed through the gas, and the calorific value of the natural gas is calculated from the optical absorption obtained on the basis of the measured intensity of the light beam after it has passed through the gas.

U.S. Pat. No. 5,822,058 teaches a system and method for optical interrogation and measurement of a hydrocarbon fuel gas utilizing a light source generating light at near-visible wavelengths. A cell containing the gas is optically coupled to the light source which is, in turn, partially transmitted by the sample. A spectrometer disperses the transmitted light and captures an image thereof. The image is captured by a low-cost silicon-based two-dimensional CCD array. The captured spectral image is then processed by electronics for determining energy or BTU content and composition of the gas.

Another known method for measuring the heating value of a fuel gas involves the use of calorimetric-based devices. In these devices, a known quantity of fuel gas is burned in a controlled flame in an adiabatic chamber. The temperature rise from the combustion process is monitored and related directly to the heating value of the gas. In a variation of the calorimetric method, a known amount of fuel gas is combusted and used to heat a known amount of water. The temperature rise of the water is then used to determine the heating value of the gas.

Gas chromatographic-based devices measure the composition of a fuel gas mixture and use that information along with known heating values of the chemical species in the gas mixture to calculate the heating value of the fuel gas mixture.

Acoustic-based methods use the velocity, velocity combined with viscosity, and attenuation of sound waves in a gas to determine the heating value of a fuel gas mixture. Yet another method involves correlating the response of an array of non-specific metal oxide sensors with the heating value of the fuel gas.

Energy can be transferred into (and out of) matter in many different ways, as heat, light, or by chemical reactions. When energy is released by matter in the form of light it is referred to as luminescence. An exception is usually made for matter that has such a high temperature that it simply glows; this is called incandescence. When energy in the form of light is released from matter because of a chemical reaction the process is called chemiluminescence. One example of a common chemiluminescent reaction is a flame, where the reaction between a fuel and an oxidant produce excited state products that emit light; however, as an example of chemiluminescence this process is complicated by the fact that incandescent particles are often also present because of the amount of heat released by the reaction; therefore, at least some of the light in a common flame comes from very hot incandescent emissions.

A better example of a chemiluminescent reaction is between nitrogen monoxide (symbol NO) and ozone ($O_3$). This reaction is routinely used to determine either ozone (using excess NO) or NO (using excess $O_3$). Nitrogen monoxide reacts with ozone to produce nitrogen dioxide ($NO_2$) in an excited state. Little of the excess energy involved in this process is released as heat; therefore, the reaction mixture and products do not incandesce to any significant degree. The reaction produces an excited state $NO_2$ which returns to a lower energy state by (in part) releasing photons of light: chemiluminescence. This electromagnetic radiation has a range of wavelengths; however, the emission is centered around 1200 nanometers (nm). The conditional words in part are included in the last paragraph because there is actually two ways excited state $NO_2$ can de-excite. One is via photon emission (chemiluminescence); another is by losing energy through collisions with other particles. This collisional process becomes more and more significant as the amount of particles available for collisions increases. In the gas phase, higher pressure means higher collision rate. This is why most gas phase chemiluminescence reactions are performed at low pressures; this increases the amount of energy released via photon emission by decreasing the amount of collisional deactivation.

SUMMARY OF THE INVENTION

It is one object of this invention to provide a method and system for measuring the energy content or heating value of a fuel gas in real-time.

It is another object of this invention to provide a method and system for measuring the energy content or heating value of a fuel gas comprising a plurality of fuel gas components.

It is a further object of this invention to provide a method and system for measuring the energy content or heating value of a fuel gas or gas mixture that overcomes the problems of conventional methods and systems for determining the heating value of a fuel gas or gas mixture.

These and other objects of this invention are addressed by a method for determining the heating value of a fuel gas or gas mixture in which a known volume of the fuel gas or gas mixture is exposed to excitation by at least one excitation source suitable for exciting at least one molecule of the fuel gas to produce chemiluminescense of at least one chemical bond of the at least one molecule. The intensity of the chemiluminescense of the at least one chemical bond is measured from which the heating value of the fuel gas is determined.

The method of this invention is based upon the fact that each chemical bond chemi-luminesces at specific, known wavelengths. In addition, the intensity of chemiluminescense for any specific bond is additive from all molecules in a gas mixture containing that bond. As a result, the measured intensity is directly and accurately related to the number of that specific bond in the fuel gas or gas mixture. Thus, knowledge of the total number of bonds per unit volume is directly and accurately related to the heating value of the fuel gas or gas mixture. The bonds to be quantified for determination of the heating value are dependent on the fuel gas component compounds. We have discovered that the number of carbon-hydrogen (C—H) bonds and carbon-carbon (C—C) bonds per unit of volume in a fuel gas or gas mixture is sufficient information to accurately determine the heating value of the fuel gas or gas mixture, e.g. natural gas, vaporized LNG and synthetic natural gas.

BRIEF DESCRIPTION OF THE DRAWINGS

These and other objects and features of this invention will be better understood from the following detailed description taken in conjunction with the drawings, wherein.

DETAILED DESCRIPTION OF THE PRESENTLY PREFERRED EMBODIMENTS

The invention claimed herein is a method and apparatus for measuring the heating value or energy content of the fuel gas or gas mixture. In this method, a stream of fuel gas or gas mixture is regulated to a desired pressure. This fuel gas or gas mixture is introduced into a specialized designed chamber in either a continuous or batch-wise manner. An excitation device operating either continuously or periodically is used to excite the molecules of the fuel gas or gas mixture. Several different excitation sources can be used including, but not limited to, an electric arc, a spark, a plasma, a laser, a flash lamp, and a pilot flame. In accordance with one preferred embodiment of this invention, the fuel gas pressure is decreased to a value below 1 atmosphere so as to enhance the excitation effect. In accordance with another preferred embodiment of this invention, the chamber comprises at least one focusing component so as to enable the detector to be exposed to the largest possible intensity of chemiluminescent gas. In accordance with one embodiment, the focusing component comprises one or more mirrors. In accordance with another embodiment, the walls of the chamber are concavely curved to provide the focusing effect.

Suitable detectors for use in the method of this invention are detectors that are tuned to measure intensity at the chemiluminescent wavelengths of the excited bonds in the ultraviolet and visible spectrums, preferably in the range of about 200 to about 600 nm. In accordance with one preferred embodiment, the detector is a CCD array. It will be apparent to those skilled in the art that other light-sensitive devices may also be employed. The tuning required to measure intensity over narrow wavelength bands may be achieved by either fabricating detectors that are sensitive to only the narrow wavelength bands of interest or by using filters in front of the detector to eliminate all wavelengths of light except the desired chemiluminescent wavelengths or wavelength bands.

Figure 1:
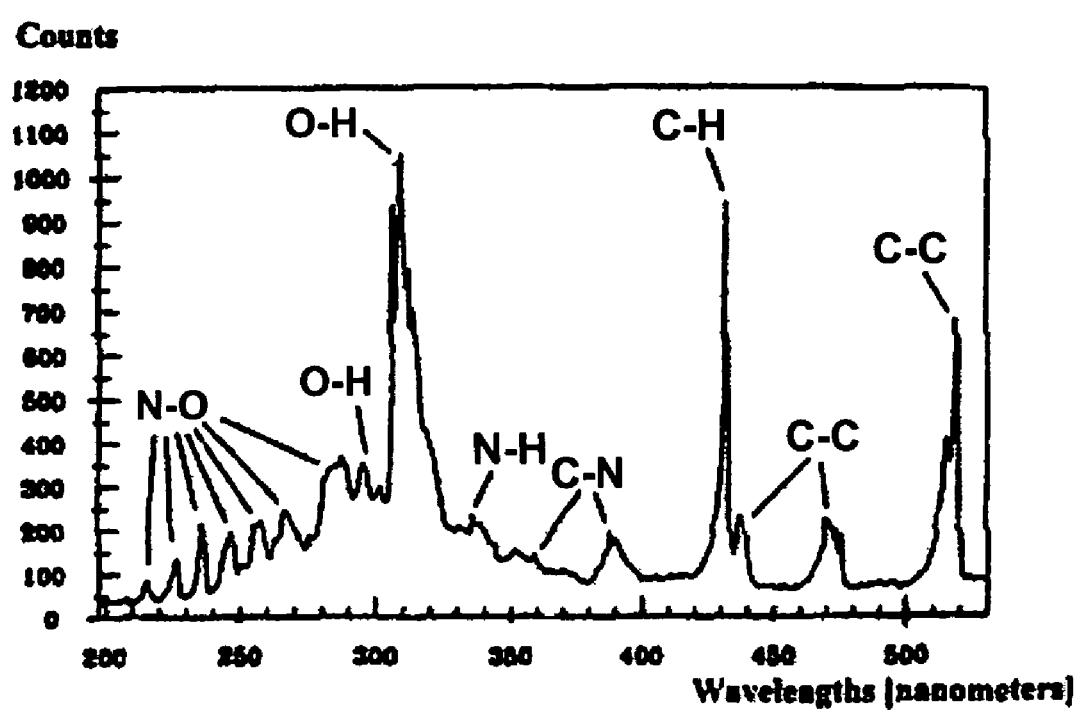
FIG. 1 is a diagram showing the locations of chemiluminescense peaks for specific chemical bonds that can be used to identify chemical radicals and chemical compounds.
Figure 2:
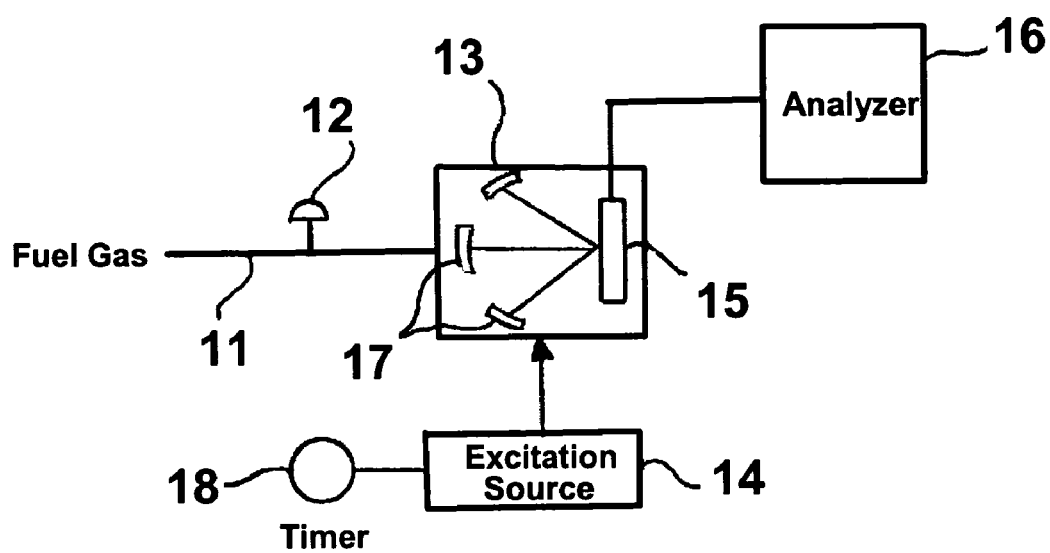
FIG. 2 is a diagram showing the components of a system suitable for measuring the heating value of a fuel gas or gas mixture.

The system for determining the heating value of a fuel gas or gas mixture in accordance with the method of this invention, as shown in an exemplary embodiment in FIG. 2, comprises a regulating component 12, for example, a flow regulator, to control fuel gas or gas mixture flow and pressure through line 11 into the sampling chamber 13. An excitation source 14 is provided for exciting the chemical bonds of the molecules comprising the fuel gas or gas mixture. If the excitation source is not continuous, a timing circuit 18 can be used to operate the excitation source 14 and then acquire intensity data from the detector 15 at the appropriate time after the fuel gas or gas mixture is acted on by the excitation component. Intensity information from the chemiluminescense of the observed chemical bonds is collected and combined mathematically in analyzer 16 to determine the heating value of the fuel gas or gas mixture, the results of which may be transmitted to a display unit. For natural gas, synthetic natural gas (SNG) and vaporized LNG containing only hydrocarbon alkane compounds and inert gases, with little or no hydrogen or sulfur-bearing compounds, only C—H and C—C ($C_2$) bond chemiluminescense intensities are needed to calculate the heating value of the fuel gas or gas mixture. FIG. 1 shows the locations of chemiluminescense peaks for specific chemical bonds that can be used to identify chemical radicals and chemical compounds (Leipertz, "Industrial Combustion Control Using UV Emission Spectroscopy," 26th International Symposium on Combustion, The Combustion Institute, 1996). For gases containing other compounds, including aromatic and double-bonded hydrocarbons, hydrogen and sulfur-bearing species, other chemiluminescense bond intensities may need to be acquired to determine the heating value of the fuel gas or gas mixture, depending upon the desired level of accuracy.

Table 1 herein below demonstrates that knowledge of the number of C—H and C—C bonds per unit volume is sufficient data to calculate the heating value of natural gas and vaporized LNG to within 0.4 Btu/ft$^3$. A simple linear correlation using these two pieces of data for a gas or gas mixture is sufficient to calculate heating value. The chemiluminescense technique of this invention can be used to measure the heating value of any fuel gas, provided that sufficient information regarding concentrations of chemical bonds is known. Fuel gases containing hydrogen, aromatic and other non-alkane hydrocarbons, and sulfur-bearing compounds require monitoring one or more chemiluminescense intensities of other bonds along with the intensities for the C—H and C—C bonds.

TABLE 1

| Fuel Gas | | Molar or Volumetric Fraction | | | | | | | | |
|---|---|---|---|---|---|---|---|---|---|---|
| | | A | B | C | D | E | F | G | H | I |
| Methane | $C_1$ | 0.9728 | 0.9590 | 0.9120 | 0.9613 | 0.8957 | 0.8918 | 0.8583 | 0.8763 | 0.8652 |
| Ethane | $C_2$ | 0.0175 | 0.0200 | 0.0410 | 0.0340 | 0.0861 | 0.0707 | 0.1257 | 0.0688 | 0.0831 |
| Propane | $C_3$ | 0.0015 | 0.0040 | 0.0110 | 0.0039 | 0.0118 | 0.0250 | 0.0133 | 0.0398 | 0.0332 |
| n-Butane | $n\text{-}C_4$ | 0.0004 | 0.0011 | 0.0023 | 0.0003 | 0.0018 | 0.0069 | 0.0008 | 0.0066 | 0.0085 |
| iso-Butane | $i\text{-}C_4$ | 0.0003 | 0.0009 | 0.0017 | 0.0004 | 0.0013 | 0.0046 | 0.0006 | 0.0084 | 0.0085 |
| n-Pentane | $n\text{-}C_5$ | 0.0001 | 0.0004 | 0.0004 | 0.0000 | 0.0000 | 0.0000 | 0.0000 | 0.0000 | 0.0000 |
| iso-Pentane | $i\text{-}C_5$ | 0.0003 | 0.0006 | 0.0006 | 0.0000 | 0.0001 | 0.0001 | 0.0000 | 0.0000 | 0.0006 |
| Hexane | $C_6$ | 0.0002 | 0.0010 | 0.0010 | 0.0000 | 0.0000 | 0.0000 | 0.0000 | 0.0000 | 0.0000 |
| Nitrogen | $N_2$ | 0.0025 | 0.0040 | 0.0200 | 0.0001 | 0.0032 | 0.0009 | 0.0013 | 0.0001 | 0.0009 |
| Carbon dioxide | $CO_2$ | 0.0044 | 0.0090 | 0.0100 | 0.0000 | 0.0000 | 0.0000 | 0.0000 | 0.0000 | 0.0000 |
| Oxygen | $O_2$ | 0.0000 | 0.0000 | 0.0000 | 0.0000 | 0.0000 | 0.0000 | 0.0000 | 0.0000 | 0.0000 |
| | sum | 1.0000 | 1.0000 | 1.0000 | 1.0000 | 1.0000 | 1.0000 | 1.0000 | 1.0000 | 1.0000 |
| Heating value, Btu/SCF | actual | 1026.56 | 1033.96 | 1047.99 | 1047.86 | 1102.51 | 1132.23 | 1133.00 | 1161.78 | 1168.28 |
| | CH conc.* | 4.02 | 4.03 | 4.05 | 4.09 | 4.23 | 4.31 | 4.31 | 4.39 | 4.40 |
| | CC conc.* | 0.03 | 0.04 | 0.08 | 0.04 | 0.12 | 0.16 | 0.16 | 0.19 | 0.20 |
| Heating value, Btu/SCF | calculated | 1026.60 | 1034.06 | 1048.11 | 1047.83 | 1102.33 | 1132.30 | 1132.58 | 1161.97 | 1168.41 |
| Error | | 0.4250 | 0.03 | 0.10 | 0.12 | −0.03 | −0.18 | 0.07 | −0.42 | 0.19 | 0.13 |

*Molar fraction

The system for measuring the heating value of a fuel gas or gas mixture dance with the method of this invention further comprises one or more means sing the chemiluminescense energy to be detected by detector 15 so as to the detector 15 to be exposed to the largest possible intensity of chemiluminescense resulting from excitation of the molecules of the fuel gas or gas mixture. In accordance with one embodiment of this invention, the focusing means comprises at least one mirror 17 disposed in sample chamber 13. In accordance with an alternate embodiment, at least one wall of the sample chamber 13 is concavely curved.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of this invention.

We claim:

1. A method for determining a heating value of a fuel gas comprising the steps of:
    exciting at least one molecule of said fuel gas, resulting in chemiluminescense of at least one chemical bond of said at least one molecule; and
    measuring an intensity of said chemiluminescense of said at least one chemical bond, resulting in determination of said heating value of said fuel gas.

2. A method in accordance with claim 1, wherein said at least one molecule is excited by a continuous excitation source.

3. A method in accordance with claim 1, wherein said at least one molecule is excited by a periodic excitation source.

4. A method in accordance with claim 1, wherein said at least one molecule is excited by an excitation source selected from the group consisting of electric arc, spark, plasma, laser, flash lamp, pilot flame and combinations thereof.

5. A method in accordance with claim 1, wherein a fuel gas absolute pressure of said fuel gas is less than about one atmosphere.

6. A method in accordance with claim 1, wherein said fuel gas is introduced into a chamber in which said at least one molecule is excited.

7. A method in accordance with claim 6, wherein said chamber comprises at least one focusing element.

8. A method in accordance with claim 7, wherein said at least one focusing element comprises at least one mirror.

9. A method in accordance with claim 7, wherein said at least one focusing element comprises at least one curved side of said chamber.

10. A method in accordance with claim 1, wherein said intensity of said chemiluminescense is measured at least one chemiluminescense wavelength in at least one of an ultraviolet spectrum and a visible spectrum.

11. A method in accordance with claim 1, wherein said intensity of said chemiluminescense is measured at least one chemiluminescense wavelength in a range of about 200 nm to about 600 nm.

12. A method in accordance with claim 1, wherein said at least one chemical bond is a carbon-hydrogen (C—H) bond.

13. A method in accordance with claim 1, wherein said at least one chemical bond is a carbon-carbon (C—C) bond.

14. A method for determining a heating value of a fuel gas comprising the steps of:
    measuring a chemiluminescense intensity of at least one chemical bond in a known volume of said fuel gas;
    determining an amount of said at least one chemical bond in said known volume of said fuel gas; and
    calculating said heating value of said fuel gas based upon said amount of said at least one chemical bond.

15. A method in accordance with claim 14, wherein said fuel gas comprises one fuel gas component.

16. A method in accordance with claim 14, wherein said fuel gas comprises a plurality of fuel gas components.

17. A method in accordance with claim 14, wherein said fuel gas comprises at least one of an alkane hydrocarbon and an inert gas.

18. A method in accordance with claim 14, wherein said chemiluminescense is produced by exciting said at least one chemical bond with an excitation source selected from the group consisting of electric arc, spark, plasma, laser, flash lamp, pilot flame and combinations thereof.

19. A method in accordance with claim 14, wherein said chemiluminescense is produced by exciting said at least one chemical bond with a continuous excitation source.

20. A method in accordance with claim 14, wherein said chemiluminescense is produced by exciting said at least one chemical bond with a periodic excitation source.

* * * * *